Figure 1:
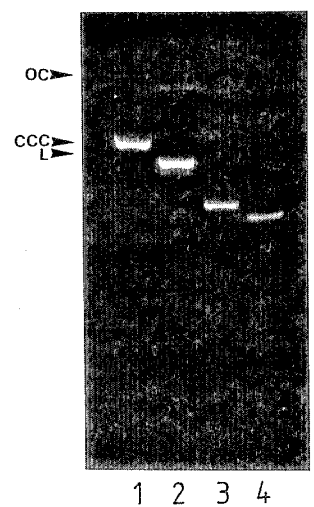

United States Patent [19]

MacPhee et al.

[11] Patent Number: 4,755,464
[45] Date of Patent: Jul. 5, 1988

[54] PREPARATION OF PLASMID DNA AND PRODUCTS THEREOF

[75] Inventors: Donald G. MacPhee, Macleod; Anthony J. Radford, Northcote; Darryl C. Reanney, Briar Hill, all of Australia

[73] Assignee: Gentech Australia Limited, South Melbourne, Australia

[21] Appl. No.: 603,239

[22] Filed: Apr. 23, 1984

[30] Foreign Application Priority Data

Apr. 21, 1983 [AU] Australia ................................ PF8994

[51] Int. Cl.⁴ ...................... C12P 21/00; C12N 15/00; C12N 1/00; C12N 1/20
[52] U.S. Cl. .................................... 435/68; 435/172.3; 435/173; 435/253; 435/320; 935/19; 935/42
[58] Field of Search ....................... 435/68, 172.3, 317, 435/173, 320; 935/19, 42

[56] References Cited

U.S. PATENT DOCUMENTS 4,311,797  1/1982  Khachatourians ............... 435/172.3

OTHER PUBLICATIONS

Sancar; A., A. M. Hack and W. D. Rupp, J. Bacteriology 137(1): 692–693, 1979.
Kapp; D. S. and K. C. Smith, J. Bacteriology 103(1):49–54 1970.
A. J. Radford, D. G. MacPhee, and D. C. Reanney, *Plasmid,* 10, 299–302(1983).
R. W. Tuveson et al., *Photochemistry and Photobiology,* 37, 109(1983).
M. H. L. Green et al., *J. of General Microbiology,* 67, 63(1971).
R. M. Tyrrell, *Int. J. Radiat. Biol.,* 25, 373(1974).

*Primary Examiner*—Thomas G. Wiseman
*Assistant Examiner*—Patricia A. Carson
*Attorney, Agent, or Firm*—Merchant, Gould, Smith, Edell, Welter & Schmidt

[57] ABSTRACT

A method for the preparation of plasmid DNA and the expression products thereof. The method provides cells, enriched in plasmid DNA and expression products thereof, which comprise chromosomal DNA which has been substantially degraded by exposing a plasmid DNA-containing organism to an effective dose of ionizing radiation.

9 Claims, 2 Drawing Sheets

PREPARATION OF PLASMID DNA AND PRODUCTS THEREOF

This invention relates to a method for the preparation of plasmid DNA and its products.

Plasmid DNA is an important tool in, for example, the recombinant genetic manipulation of microorganisms, in which the objective is to introduce into a cell, 'foreign' genetic material (DNA) the expression of which enables that cell to produce substances, for example, biologically active molecules, whether having enzymatic, antigenic antibiotic, hormonal, antiviral, or having any other physiological or biological activity, which the cell in its 'natural', i.e. unmodified state, is unable to produce.

Thus, when a plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it.

In biotechnological processes involving plasmid DNA, and the expression products thereof, industrial scale production is limited by the small amount of plasmid DNA, as compared with chromosomal DNA in a selected cell. For example where the plasmid carries cloned genes of commercial interest, the amount of product is chiefly determined by the number of copies of the gene or genes in both DNA and RNA forms which are available in the system. The efficiency of the process is ultimately dependant on the proportion of added nutrients/raw materials, which must be consumed to sustain growth of the producer organism rather than go to make up the product itself. Accordingly in the prior art attempts have been made to separate plasmid and chromosomal DNAs and to generate cells containing only plasmid DNA.

As used herein in the specification and claims, a plasmid is defined as any small amplifiable ring of DNA found in any kind of cell whether of plant, fungal or microbial origin.

Plasmid and chromosomal DNAs have conventionally been separated on cesium chloride (CsCl) gradients by exploiting the differences in buoyant density between the ethidium bromide-saturated, closed-circular plasmids and linear chromosomal fragments. This is a time-consuming method, which is expensive in both materials and equipment. While a number of rapid techniques for the extraction of plasmid DNA have been developed, few, if any, consistently produce chromosome-free plasmid DNA, although they do greatly reduce the proportion of chromosomal material in the preparation.

One solution to this problem is to propagate plasmids in cells in which chromosomal DNA has been degraded. UV irradiation of uvrA phr cells has been found to inactivate chromosomal DNA without impairing the ability of these cells to support the amplification of small plasmids [Sancar, A., Hack, A. M. and W. D. Rupp, (1979), "Simple method for identification of plasmid-coded proteins.", J. Bacteriol. 137: 692–693]. Chromosomal DNA in these excision-deficient 'maxicells' is degraded, most probably because the gaps left opposite dimers during replication act as targets for the recB/recC nuclease [Clark, A. J., (1973), "Recombination deficient mutants of E. coli and other bacteria.", Annual Review of Genetics 7: 67–86.].

However, the UV/maxicell technique suffers from three main disadvantages for routine use. Firstly, it is necessary either to introduce a phr mutation into the strain(s) of interest, or to work in the dark (a mutation in the phr gene should serve to eliminate photoreactivation). Secondly, even for work in the dark, optimal use of the technique normally requires the construction of a double mutant (uvr recA) of each plasmid-containing strain which is to be used, or else transformation of the plasmid of interest into such a double mutant. Thirdly, the cells must normally be exposed to the UV source as a thin film in order to maximise the chances of every cell receiving a lethal dose of radiation. This requirement generates handling difficulties and lowers the volume of culture which can be processed in any one experiments.

Accordingly, it is an object of the present invention to overcome, or at least alleviate some of the difficulties related to the prior art.

According to the present invention there is provided a method of preparing cells enriched in plasmid DNA, and expression products thereof, substantially free of chromosomal DNA, which method comprises
(a) providing a plasmid DNA-containing organism and
(b) exposing the organism to an effective dose of ionizing radiation.

The treatment may be such that non-dividing cells which can sustain the multiplication of plasmids are produced.

The plasmid DNA-containing organisms may be selected from micro-organisms, fungi, plant and animal cells. The cells may be present in a packed cell form although a liquid culture may be used. The micro-organisms may be bacteria cells. The bacteria cells may be selected from E.coli, Bacillus or Pseudomonas sp or Streptococci. Repair and/or recombination-deficient bacterial cells, i.e. cells genetically deficient in their ability to undertake repair/recombination processes are preferred. Particularly preferred are recA mutants of E. coli and rec-type mutants of Bacillus, Pseudomonas and Streptococcus.

The invention also encompasses methods of damaging or inactivating the cell's repair/recombination systems by treatment of the target cells with chemical agents before, during or after the gamma-irradiation. This would enable the technique to be applied to any kind of cell in the absence of induced genetic lesions.

The ionizing radiation utilised in step (b) of the method according to the present invention may take the form of x-rays or gamma rays. The ionizing radiation apparently generates gaps directly in the DNA of irradiated recA cells and hence renders that DNA highly susceptible to recB/recC nuclease attack, equivalent to what has been reported in respect of both Uvr+ and uvr strains of E. coli [Clark, A. J., Chamberlain, M., Boyce, R. P. and Howard-Flanders, P., (1977), "Abnormal metabolic response to ultraviolet light of a recombination-deficient mutant of Escherichia coli K12.", J. Mol. Biol. 19: 442–454; and Kapp, D. S. and Smith K. C., (1970), "Repair of radiation-induced damage in Escherichia coli.", J. Bact. 103(1): 49–54.].

The ionizing radiation is preferably gamma radiation. The gamma radiation source may be a cobalt 60 source. The radiation dosage may be sufficient to eliminate substantially all chromosomal material from the DNA preparations. Doses of between approximately 0.1 to 0.25 kgy are preferred. For example 0.2 kgy of gamma-irradiation may be used.

In a preferred aspect of the present invention there is provided a method of preparing plasmid DNA substantially free of chromosomal DNA which method comprises (a) providing a recA strain of bacteria, and
(b) exposing the recA bacteria to approximately 0.1 to 0.25 kgy of gamma-irradiation.

In accordance with a further aspect of the present invention the methods of preparing plasmid DNA may further comprise (a') subjecting the recA bacteria to a plasmid yield-increasing treatment prior to irradiation. The plasmid yield increasing treatment may comprise treating the bacteria with an antibiotic or antibiotics.

Antibiotics may be used to enhance the copy number of the plasmid. The antibiotic may be selected from spectinomycin and the like and mixtures thereof.

In a still further preferred aspect of the present invention there is provided a method for synthesising expression products of plasmid DNA which method comprises (a) providing
 (i) a DNA fragment encoding desirable characteristics, and
 (ii) an organism containing a plasmid,
(b) cloning the DNA fragment into the plasmid,
(c) transforming or transfecting a suitable recipient organism with the recombinant plasmid.
(d) exposing the organism containing the plasmid to an effective dose of ionizing radiation such that non-dividing cells which are substantially free of chromosomal DNA and can sustain the multiplication of plasmids are produced, and
(e) maintaining the processed cells in a suitable nutrient medium.

Preferably the method further comprises after the transformation step (c)

(c') growing the cells to a desired concentration. The expression products produced thereby may include RNA and expressed proteins. The products may be suitable for use as enzymes, antibiotics, antivirals, hormonal treatments and the like.

In a particularly preferred form the irradiation step (d) and maintenance step (e) may be undertaken in a packed cell form, e.g. immobilised cell system although a liquid culture form may be used. It will be understood that an advantage of the use of ionizing radiation is that the penetrating ability thereof allows significant volumes of packed cells rather than liquid cultures to be treated for plasmid amplification expression. This will provide a further substantial scale-up factor in the amount of product produced.

It will thus be understood that the method according to the present invention allows for the preparation of plasmid DNA and the encoded products of that plasmid DNA essentially by destroying the cell chromosomes of selected cells with ionising radiation whereby those cells are enriched in plasmid DNA and consequently in the products of that DNA.

The method also thus allows the production, on an industrial scale, of cells containing only plasmid DNAs together with any foreign genes whatsoever that may have been cloned into these plasmid DNAs. The ability of the processed cells to produce plasmid encoded proteins from any source whatsoever is thus substantially improved.

We have thus found that ionizing irradiation treated recA bacteria, bacterial cells, exemplified by gamma-irradiated recA bacteria, are efficient producers of undamaged plasmid DNA under conditions at which at most only trace amounts of chromosomal DNA remain undegraded. The gamma-irradiation technique has a number of advantages over other methods for preparing substantially pure plasmid DNA, as follows: (1) there is little, if any, contamination of DNA preparation by chromosomal DNA owing to extensive degradation of the irradiated DNA by endogenous nucleases; (2) there is no need to introduce a uvr mutation to the host bacteria, whereas there is when UV is used to inactivate the chromosome; (3) the method is extremely simple to work with, since operations are not limited by considerations of volume and cell density; and (4) there is no need to transfer material from container to container. Also, yields of plasmid DNA obtained by the gamma-irradiation technique compare favourably with those obtained by other methods.

The present invention will now be more fully described with reference to the accompanying drawings and examples. It should be understood, however, that the matter following is illustrative only and should not be taken in any way as a restriction on the generality of the description above.

FIG. 1 of the accompanying drawings illustrates electrophoresis of undigested plasmid DNA from gamma-irradiated cells. Tracks (1), (2) and (3) are pBR322 containing fragments of transposon DNA ranging in size from 5.1 kb (1) and 4.3 kb (2), to 2.0 kb (3) cloned in the Hind III site. All were extracted from E. coli DG1210. Track (3) is pBR325 extracted from E. coli HB101. L-linear DNA; CCC-covalently closed circular DNA; OC-open circular DNA. Arrows apply to Track (1) only.

Figure 2:
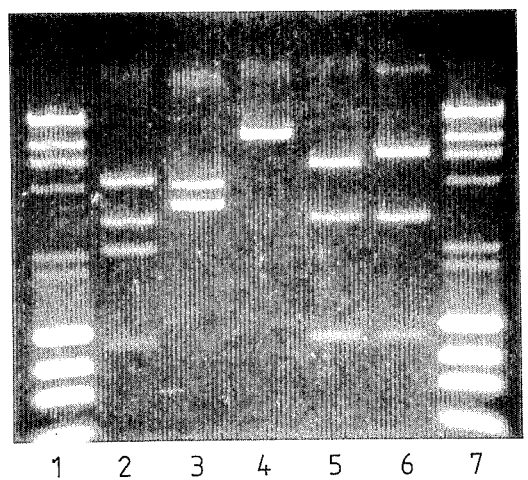

FIG. 2 of the accompanying drawings graphically illustrates the restriction digests of plasmids from gamma-irradiated cells, with the following explanations: Track (1) and (7) λc1857 Hind III plus ΦX174 Hae III; (2) pBR325:TN3405 Eco RI, Pst; (3) Pst I, Hind III; (4) Pst I; (5) Eco R1, Hind III; (6) Eco R1. Plasmid DNA extracted from E. coli HB101.

In the examples set out below reference is made to bacterial strains and plasmids specified as follows:

| BACTERIAL STRAINS AND PLASMIDS | |
|---|---|
| Bacterial strains | |
| E. coli K12 | |
| HB101 | pro leu thi lacY hsdR endA recA rpsL20 ara-14 galK2 xyl-5 mtl-1 supE44 |
| J5-3 | met pro |
| E. coli WP2 | |
| DG1210 (trp)recA uvrA | |
| Plasmids | |
| RP1 | $Km^R$, $Cb^R$, $Tc^R$, $Tra^+$ |
| pBR322 | $Cb^R$, $Tc^R$ |
| pBR325 | $Cm^R$, $Cb^R$, $Tc^R$ |
| pBR 325::Tn3405[a] | $Cm^R$, $Cb^R$, $Tc^{Ra}$ |

[a]Tn3405 is a recently discovered cryptic transposable element (Radford and Reanney, unpublished).

EXAMPLE 1 ml samples of overnight cultures of plasmid, carrying derivatives of E. coli recA strains (either HB101 or DG1210, Table 1 above), were inoculated into 10 ml aliquots of nutrient broth containing ampicillin (100

μg), the ampicillin being added to ensure maintenance of plasmids. After shaking for 3 hr at 37° C., spectinomycin was added to a final concentration of 100 μg/ml. The culture was then returned to the shaker for a further 3 h. In this context, because it increases plasmid yield, the addition of spectinomycin provides the advantages of increasing the probability that at least one undamaged (small) plasmid will survive the gamma-irradiation. A further advantage is that, should a cell with an intact chromosome survive the radiation treatment, it is unlikely to multiply if protein synthesis is inhibited.

The culture was then exposed to a $^{60}$Co-λ source (dose approximately 0.45 kGy/hour) for 30 min and returned to the shaker for 1 h whereupon 2 ml of nutrient broth containing cycloserine was added to give a final cycloserine concentration of 100 μg/ml. Cycloserine causes growing cells to lyse, while the extra broth enriches the depleted medium, encouraging further growth. The culture was left on the shaker at 37° C. overnight. The next morning, plasmid DNA was extracted by the rapid technique of Currier and Nester [Currier, T. C. and E. W. Nester, (1976), "Isolation of covalently closed DNA of high molecular weight from bacteria.", Anal. Biochem. 76: 431-441.]. Cells from the 12 ml culture were pelleted in a bench centrifuge, then washed and resuspended in 2 ml of TE8 buffer (50 mM TRIS, 20 mM EDTA, pH 8.0). A further centrifugation and resuspension was carried out, then a 200 μaliquote of protease E (Sigma, Type XIV) (5 mg/ml self digested for 1 hour) was added, followed by 200 μl of 10% SDS. This mix was left at 37° C. for 45 min after which 100μl of 2 M NaOH was added. The mixture was stirred by gentle inversion of 15 min then 200 μl of 2 M TRIS pH 7.0 was added to lower the pH. 300 μl of 5 M NaCl was also added. This solution was mixed with 3 ml phenol that had been equilibrated with 3% NaCl and stirred by inversion for 5 min. The phenol was removed by 10 min centrifugation at 2000 g and the aqueous phase drawn off. To the aqueous phase 380 μl of 3 M sodium acetate was added together with 500 μl of 5 M NaCl and 2.5 volumes of cold ethanol. The mixture was shaken and left at −20° C. for at least 2 hr. The plasmid DNA could then be pelleted in a bench centrifuge by centrifuging at 2000 g for 10 min. The pellet was washed with 70% ethanol to remove residual phenol and resuspended in water.

Restriction and other enzymes were obtained from Boehringer Mannheim (Australia) Ltd, and were used as directed by the manufacturer. Agarose gel electrophoresis was in 1% submarine gels, at 80 volts for 3-5 hours.

To assess the susceptibility of the test bacteria to gamma-irradiation, E. coli K12 strains DG1210, HB101 and J5-3 were irradiated during late log phase with progressive doses of gamma-rays (dose rate, 0.45 kGy/h). As expected, the recA strains were significantly more sensitive than the wild-type organism, for example, at 15 min the percentage of DG1210 survivors was 0.025% of that for J5-3 cells.

We have found that doses of between 0.1-0.25 kGy, for instance, 0.2 kGy of gamma-irradiation is sufficient to eliminate virtually all chromosomal material from DNA preparations obtained from recA cells. FIG. 1 of the accompanying drawings shows that there was no visible chromosomal band in the undigested DNA preparations from the gamma-irradiated bacteria—see Tracks 1-4, and no chromosomal 'smear' could be seen in preparations treated with restriction nucleases—see Tracks 2-6 of FIG. 2 of the accompanying drawings. A considerable amount of RNA remained in the preparations but this can readily be removed by ribonuclease treatment. Unlike the case with CsCl gradients, there is no selection for supercoiled DNA, so linear and open circular forms of plasmid DNA may be present in low quantities—see Tracks 1 and 2 of FIG. 1.

Both 10 ml and 100 ml culture samples used in our experiments consistently yielded 1 μg of DNA per ml of original culture with derivatives of pBR325 and pB322. This corresponds to a value of about 1 mg per liter of culture, which compares favourably with the yields obtained by the conventional techniques.

To ascertain whether the plasmid DNA extracted from gamma-irradiated recA cells had been unacceptably damaged by the radiation, pBR325:Tn3405 DNA was digested with a variety of restriction nucleases, singly and in combination, and electropheresed on agarose gels. Results—see FIG. 2 of the accompanying drawings, showed that the plasmid profiles were identical to those obtained from unirradiated cells (data not shown). These data indicate that there were no significant gross deletions, duplications or other sequence aberrations in either plasmid or transposon DNA.

Plasmid DNA from gamma-irradiated cells has been successfully used by us in nick translation preparations. Also pBR325 DNA isolated from gamma-irradiated cells has been used by us to transform HB101 cells using ampicillin selection. Transformation frequencies were similar to those obtained with DNA made by conventional CsCl methods. The fact that the plasmids retained their original resistance phenotypes indicates that no damage to the relevant genes had occurred.

Since the target size of a plasmid exposed to gamma-radiation increases with the molecular weight of the plasmid, the upper size limit of plasmids which can be efficiently propagated by means of the present method can be readily determined by the skilled person conducting routine tests for the purpose. The largest replicon used in our experiments was pBR325:Tn3405, the calculated size of which is ca 11 Kilobase pairs of DNA.

The gamma-irradiation method of the present invention will be seen to have a number of advantages over the UV 'maxicell' technique of Sancar et al, supra. Thus, because of the penetrating nature of gamma-rays, it is not necessary to irradiate the cells in a thin surface film, as is the case with the UV method. This makes the present method less exacting to perform than the UV treatment, and, related to our experiences and those of others with the UV method, less prone to failure than is the UV method. Significantly, because the cells do not need to be irradiated in thin films, it is possible to use almost any volume of bacterial culture, the only limiting factor in essence being the capacity of the gamma-ray source to accommodate the amount of culture to be treated. Also, because the effects of gamma-irradiation are not limited by cell density, it is possible to expose cells to gamma-radiation in the form of packed cell pellets rather than as liquid cultures. This concentration factor would raise the number of cells which can conveniently be treated, by several orders of magnitude.

Another advantage is the inherent simplicity of the method itself in terms of ease of handling and operation. All treatments of the cells can be performed in one container. As most chromosomal DNA has been removed by the time the cells are lysed, there is little chance of overloading the system during phenol extraction and producing a difficult-to-work-with gelantinous aqueous phase, hence a large number of cells can be lysed in a small volume. Also, as with the 'maxi-cell' technique of Sancar et al, supra, the gamma-irradiation technique can readily be used for studies on plasmid-encoded RNAs and proteins.

Although we have demonstrated the method of the present invention above, using *E. coli* as the host for plasmids said method is applicable to any species of bacteria in which rec-type mutants are available. A rec mutated cell is desirable for successful operation of the present method because wild-type (non-mutant) cells can often repair damage induced by radiation, the recA+ gene product or similar gene products being involved in such repair. However the technique may be generally applied to non-mutated wild-type, cells of any type, e.g. conditions such as gamma-irradiation in the presence of suitable chemicals e.g. bleomycin nitrofuran antibiotics may be used when plasmids only are preferentially replicated or expressed even in rec+ cells, or to polA mutants (which also degrade their chromosonal DNA following exposure to ionizing radiation).

EXAMPLE 2

The following example illustrates a use of the method according to the present invention to produce plasmid encoded proteins from gamma-irradiated bacteria. The example also investigates effects of gamma ray dosage on protein expression.

*Escherichia coli* HB101 containing the plasmid cloning vector pBR325 was chosen as the test organism for irradiation. Plasmid pBR325 carried three resistance factors, to tetracycline, chlormaphenical and penicillin. The penicillin resistance is mediated by the production of a $\beta$-lactamase ($\beta$-lac) enzyme, which inactivates penicillin by breaking the $\beta$-lactam ring of the antibiotic. As $\beta$-lac is produced constitutively (i.e. continually, with no need of a specific inducer) the amount of enzyme produced should be directly proportional to the gene copy number.

Consequently, *E. coli* HB101 pBR325—which is a recA cell and suitable to the gamma cell technique—was tested for $\beta$-lac activity after varying levels of gamma-irradiation. Cell lysates were tested rather than whole cells, as enzyme activity could be masked by factors such as cell wall permeability if intact cells were used. This also permits estimation of $\beta$-lac at the time of lysis and eliminates the possibility of growth and cell division by untreated bacteria.

Activity of $\beta$-lac was assayed by incubating lysate with a known amount of sodium benzylpenicillin, then measuring the amount of active penicillin left in the mix by biological assay. The lysate-penicillin mixture was serially diluted in broth and the presence of penicillin ascertained by adding a penicillin-sensitive test organism, *Micrococcus luteus*, to the various organisms. Growth in the tube indicated that penicillin had been inactivated to below the M.I.C. of *M. luteus*.

Also determined was the cell density of the normal and gamma-treated cultures and the total protein concentration of the lysates.

*E. coli* HB101 pBR325 cells were treated as per the gamma technique for 1, 2, 5, 15 and 30 minutes at a dose rate of 0.42 kGy/hr. Controls included an *E. coli* of HB101 pBR325 grown to the same state as the gamma-treated cells were immediately prior to irradiation, and an *E. coli* J5-3 culture containing no $\beta$-lactamase genes. Lysates were prepared by centrifuging 10 mls of culture, resuspending the cell pellet in 3 ml of sterile saline, adding lysozyme to 0.1 $\mu$g ml$^{-1}$ and then sonicating.

The assay was conducted as follows: lysates were mixed with penicillin solutions, incubated, and the lysate/penicillin mix chloroform extracted then serially diluted in nutrient broth. The sensitive *M. luteus* was then added to each broth. The penicillin solutions were diluted in broth before the addition of filter sterilized lysate and the incubation step.

Detailed methods are set out below.

1. *E. Coli* HB101 containing pBR325 was grown for 90 minutes to log phase and 1/10 diluted culture incubated with 25 microgram per liter, Chloramphenicol all in nutrient broth (NB). The cells were treated with gamma-irradiation at .42 kGy per hour for 1, 2, 5, 15 and 30 minutes. The cultures were kept in the dark and put on a shaker for 2 hr at 37° C., 2 ml of NB with 2000 $\mu$g ml$^{-1}$ fresh D-cycloserine was then added. The culture was left overnight at 37° C. with shaking.

Untreated *E. coli* HB101 cells with pBR325 and *E. coli* J5-3 were log phase 90′ cultures of 1/10 diluted overnight cultures.

2. Cells were centrifuged and resuspended in 3 ml sterile saline. Optical density measurements were taken at 560 nm and 600 nm.

3. To all cultures was added lysozyme, 30 $\mu$l of 10 mg.ml$^{-1}$. This was to weaken rather than break the cell walls. Each culture was then lysed by a 30 second burst (setting 3, high power, 4 microns) of an ultrasonic disintegrator. This was done on ice and the lysate immediately packed in ice.

4. 50 $\mu$l lysate was added to 600 $\mu$l of 1000 units and 200 units ml$^{-1}$ sodium benzylpenicillin. This was left for one hour at 37° C.

5. The mixture was then extracted with 500 $\mu$l of chloroform, vortexing once every 2 minutes for 10 minutes. (Sodium benzylpenicillin is only sparingly soluble in chloroform.) Chloroform was separated by centrifugation, and the aqueous phase removed and left at 68° C. for 10′ to distil out residual chloroform.

6. Penicillin was diluted from 400 units ml$^{-1}$ through 10 doubling dilutions in NB and 10 $\mu$l of sterile lysate was added to 1 ml of each dilution. This was incubated one hour at 37° C., followed by 10′ at 68° C., after which 30 $\mu$l of *M. luteus* in broth culture added to each dilution.

7. Tubes were incubated overnight at 37° C. with shaking, and growth recorded in the morning. Where growth did occur, streaks of the culture on nutrient agar were performed to confirm that the organism was *M. luteus*.

8. Electrophoresis was in a 15% discontinuous polyacrylamide gel following the method of Laemmli.

The results of the assay are set out in Table 1. It is clear from Table 1 that the greatest $\beta$-lac activity of the gamma-irradiated cells was in the culture given a 5 minute dose. Activity per cell in this culture was in the range of 15–30% of an untreated culture, adjusting for cell numbers by using absorption to estimate cell density (Table 2).

Examination of Total Proteins

Total protein concentration of filtered cell lysates was estimated by the Lowry method. There was little variation between any of the lysates (Table 3). However, the Lowry method will not discriminate between functional, intact proteins and protein degradation products such as poly-oligopeptides.

Figure 3:
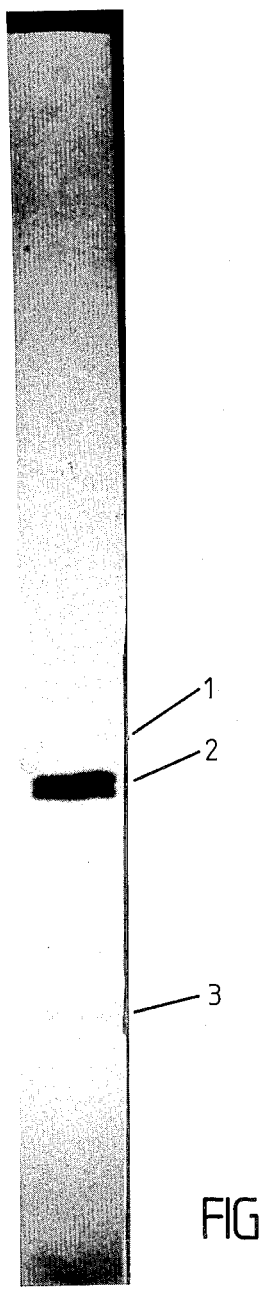

That the plasmid coded proteins are the only new proteins being produced in gamma-maxi cells is illustrated in FIG. 3. Here cells that have received a 30 minute dose at 0.45 kGy/hr have been used to examine new protein synthesis. The cells used are *E. coli* HB101 containing plasmid pBR322, which in itself has a cloned insert of 5.2 kb pairs of DNA in the HindIII site. Coded on this Figure are β-lactamase 1, two cryptic polypeptides 2 and organomercurial lyase 3.

After gamma maxi-cell treatment new proteins have been labelled by the addition of $^{35}$S-methionine to the medium. Only proteins synthesized after addition of the methionine will be radioactively labelled. Cells were then lysed and the lysate applied to a polyacrylamide gel. As can be seen from FIG. 3, only the designated plasmid-coded proteins have been synthesized in the gamma-treated cells.

Comments

Levels of β-lac in *E. coli* HB101 pBR325 are depressed after gamma-maxi-cell treatment. This is not surprising, as radiation will probably affect the plasmids to a slight degree as well as the chromosomal DNA. What may compensate for this is an increase in plasmid copy number in treated cells.

On a per cell basis the greatest level of active β-lac found in a gamma-treated cell was between 15–30% of an untreated cell.

TABLE 1

| TUBE | 1 | 2 | 3 | 4 | 5 | 6 | 7 | 8 | 9 | 10 | 11 |
|---|---|---|---|---|---|---|---|---|---|---|---|
| Concentration of penicillin gamma-irradiated lysate of *E. coli* HB101 cells + plasmid pBR325 Minutes of treatment with gamma-irradiation | 4000 | 2000 | 1000 | 500 | 250 | 125 | 62 | 31 | 16 | 8 | 4 |
| 1 | − | − | − | − | − | − | − | − | − | − | − |
| 2 | − | − | − | − | − | − | − | − | − | − | − |
| 5 | − | − | − | − | − | − | ½+ | + | + | + | + |
| 15 | − | − | − | − | − | − | − | − | − | − | − |
| 30 | − | − | − | − | − | − | − | − | − | − | − |
| *E. coli* HB101 cells + pBR325 unirradiated | − | − | − | − | + | + | + | + | + | + | + |
| *E. coli* J5-3 unirradiated | − | − | − | − | − | − | − | − | − | − | − |
| Penicillin control | − | − | − | − | − | − | − | − | − | − | − |

+ = Growth
− = No Growth

TABLE 2

| | Optical density of cultures | |
|---|---|---|
| CULTURE | A° 560 | A° 600 |
| 1 minute | 0.906 | 0.793 |
| 2 minute | 0.989 | 0.893 |
| 5 minute | 1.033 | 0.931 |
| 15 minute | 0.870 | 0.846 |
| 30 minute | 1.164 | 1.073 |
| J-53 | 0.950 | 0.849 |
| HB101 pBR325 | 1.402 | 1.288 |

TABLE 3

| Estimates of protein concentrations by Lowry method | | |
|---|---|---|
| 1.0 mg ml$^{-1}$ protein | A° 575 | A° 750 |
| Standard | 0.480 | 0.606 |
| J5-3 | 0.082 | 0.149 |
| HB101 pBR325 gamma | 0.063 | 0.125 |

TABLE 3-continued

| Estimates of protein concentrations by Lowry method | | |
|---|---|---|
| 1.0 mg ml$^{-1}$ protein | A° 575 | A° 750 |
| 1 minute | 0.068 | 0.131 |
| 2 minute | 0.051 | 0.109 |
| 5 minute | 0.055 | 0.121 |
| 15 minute | 0.072 | 0.133 |
| 30 minute | 0.070 | 0.131 |

What is claimed is:

1. A method for preparing bacterial cells enriched in plasmid DNA and expression products thereof, substantially free of undegraded chromosomal DNA which method comprises:
   (a) providing a repair and recombination deficient bacterial strain;
   (b) exposing the strain to a total dose of about 0.01–0.25 kGy of gamma irradiation such that non-dividing cells are produced which can sustain the multiplication of plasmids and which comprise chromosomal DNA which has been substantially degraded; and
   (c) recovering the non-dividing bacterial cells so produced.

2. A method according to claim 1 wherein the bacterial cells are present in a packed cell form.

3. A method according to claim 1 wherein the bacterial strain is selected from recA mutants of *E.coli*.

4. The method according to claim 1 wherein the source of gamma irradiation is Cobalt 60 ($^{60}$Co).

5. A method for synthesizing expression products of plasmid DNA which method comprises;
   (a) providing
      (i) a DNA fragment encoding desirable characteristics, and
      (ii) an organism containing a plasmid,
   (b) cloning the DNA fragment into the plasmid,
   (c) transforming or transfecting a repair and recombination deficient bacterial strain with the recombinant plasmid,
   (d) exposing the bacterial strain containing the plasmid to a total dose of about 0.01–0.25 kGy of gamma irradiation such that non-dividing bacterial cells are produced which can sustain the multiplication of plasmids and which comprise chromosomal DNA which has been substantially degraded, and (e) maintaining the processed bacterial cells in a suitable nutrient medium.

6. A method according to claim 5 further comprising (c') after cloning step (b) growing the plasmid-containing cells to a desired concentration.

7. A method according to claim 6 wherein the cells are present in a packed cell form.

8. A method according to claim 6 wherein the bacteria is a recA strain of *E. coli*.

9. The method according to claim 5 wherein the source of gamma irradiation is Cobalt 60 ($^{60}$Co).

* * * * *